United States Patent [19]

D'Antonio et al.

[11] Patent Number: 4,715,855

[45] Date of Patent: Dec. 29, 1987

[54] DRY BOTTLE DRAINAGE SYSTEM

[75] Inventors: Nicholas F. D'Antonio; Nicholas J. D'Antonio, both of Liverpool, N.Y.

[73] Assignee: Pfizer Hospital Products Group, Inc., New York, N.Y.

[21] Appl. No.: 642,564

[22] Filed: Aug. 20, 1984

[51] Int. Cl.$^4$ .............................................. A61M 1/00
[52] U.S. Cl. ..................................... 604/320; 604/119; 73/716; 73/756
[58] Field of Search .............. 604/317, 318, 319, 320, 604/321, 324, 118, 119, 120; 137/205, DIG. 8, 517, 514.7; 138/45, 46; 73/716, 756; 116/270, 271, 268, 70

[56] References Cited

U.S. PATENT DOCUMENTS

| | | | |
|---|---|---|---|
| 869,323 | 10/1897 | Nolan | 137/541 |
| 1,074,306 | 9/1913 | Wolf | 73/716 |
| 2,280,992 | 4/1942 | Wright et al. | 604/119 |
| 2,286,841 | 6/1942 | Smith | 137/539 |
| 2,764,894 | 10/1956 | Faxen | 116/270 |
| 3,545,440 | 12/1970 | Mishkin et al. | 604/321 |
| 3,763,884 | 10/1973 | Grassi et al. | 137/517 |
| 3,863,671 | 2/1975 | Heimann | 137/514 |
| 4,468,226 | 8/1984 | Kurtz et al. | 604/318 |
| 4,533,353 | 8/1985 | Akiyama | 604/321 |

FOREIGN PATENT DOCUMENTS

| | | | |
|---|---|---|---|
| 2500993 | 7/1975 | Fed. Rep. of Germany | 604/317 |
| 2082071 | 6/1980 | United Kingdom | 604/319 |

Primary Examiner—Richard C. Pinkham
Assistant Examiner—Matthew L. Schneider
Attorney, Agent, or Firm—D. Peter Hochberg

[57] ABSTRACT

A fluid drainage system includes a suction chamber and a collection chamber. The suction chamber includes a suction regulator comprised of first and second chambers separated by a divider. An opening in the divider has a biased closing member associated therewith for opening or closing the opening according to the pressure differential between the chambers. A dash pot is connected to the closing member for damping the force on the closing member. The drainage system further includes devices for measuring the patient airflow, patient negativity and imposed suction. Those devices consist of diaphragms having dials connected thereto such that movement of the diaphragm results in movement of the dial and thereby indicating a change in one of the above noted variables. As an alternative, the drainage system includes a venturi meter for measuring airflow. Finally, the system contains an anti-spill device that prevents the spilling of fluids from the collection chamber to other chambers in the device.

10 Claims, 12 Drawing Figures

DRY BOTTLE DRAINAGE SYSTEM

BACKGROUND OF THE INVENTION

This invention relates to fluid pressure regulating systems, including systems for measuring gas pressure and for controlling the pressure of the gas. The invention further relates to wound drainage systems for draining fluids from medical patients, such as from the chest cavity, by means of gas pressure differentials using low pressure gas systems.

In many situations involving gases, it is important and often mandatory to measure the pressure of the gas. A typical example of the need to measure gas pressure exists in hospitals, where the vacuum or suction distributed in the hospital from a central vacuum supply must be monitored as it is used. Such suction is used, for example, in conjunction with wound drainage devices, where fluids such as blood, water and gas from a wound victim's pleural cavity are withdrawn using a pressure differential established between the suction source and the internal pressure in the victim. Such suction pressure and pressure differentials must be precisely measured because of the dangerous conditions which could result if unduly high or low pressure differentials should occur. In this application as in many other pressure measuring applications, it is desirable to incorporate a pressure measuring device which is compact, which makes the pressure measurements with precision, which is capable of functioning reliably for long periods of time, and which is economical to manufacture. Presently available gas pressure measuring devices which have the desired reliability and precision are generally expensive because of their intricacy or bulk due to their incorporation of manometer tubes. Wound drainage systems incorporating manometers having water whose level indicates fluid pressure are inconvenient because of the need to add water prior to use, as well as because of their size and weight.

For many years, a standard apparatus for performing the evacuation of the pleural cavity was an underwater seal drainage system known as the "3-bottle set-up". The 3-bottle set-up consists of a collection bottle, a water seal bottle and a suction control bottle. A catheter runs from the patient's pleural cavity to the collection bottle, and the suction bottle is connected by a tube to a suction source. The three bottles are connected in series by various tubes to apply a predetermined suction to the pleural cavity to withdraw fluid and air, and discharge the same into the collection bottle. Gases entering the collection bottle bubble through water in the water seal bottle. The water in the water seal also prevents the back flow of air into the chest cavity.

The 3-bottle set-up lost favor with the introduction of an underwater seal drainage system sold under the name "Pleur-evac" in 1966 by Deknatel Inc., the predecessor of the Deknatel Division of Howmedica Inc. U.S. Pat. Nos. 3,363,626; 3,363,627; 3,559,647; 3,683,913; 3,782,497; 4,258,824; and Re. 29,877 are directed to various aspects of the Pleur-evac system which has been marketed over the years The Pleur-evac system provided improvements that eliminated various shortcomings of the 3-bottle set-up. These improvements have included the elimination of variations in the 3-bottle set-up that existed between different manufacturers, hospitals, and hospital laboratories, such variations including bottle size, tube length and diameter, stopper material and the like. Various inefficiencies and dangers have existed in the 3-bottle set-up resulting from the many separate components and the large number (usually 16 or 17) of connections, such as pneumothorax which may result from the loss of the water seal in the water seal bottle if suction were temporarily disconnected, and possible build-ups of positive pressure which could cause tension pneumothorax and possible mediastanal shift. Another serious shortcoming of the 3-bottle set up is danger of incorrect connection and the time necessary to set the system up and to monitor its operation.

Among the features of the Pleur-evac system which provide its improved performance are employment of 3-bottle techniques in a single, pre-formed, self-contained unit. The desired values of suction are established by the levels of water in the suction control bottle and the water seal bottle, which levels are filled according to specified values prior to the application of the system to the patient. A special valve referred to as the "High Negativity Valve" is included which floats closed when the patient's negativity becomes sufficient to threaten loss of the water seal. Also, a "Positive Pressure Release Valve" in the large arm of the water seal chamber works to prevent a tension pneumothorax when pressure in the large arm of the water seal exceeds a prescribed value because of suction malfunction, accidental clamping or occlusion of the suction tube. The Pleur-evac system is disposable and helps in the battle to control cross-contamination.

Despite the advantages of the Pleur-evac system over the 3-bottle set-up and the general acceptance of the device in the medical community, there has remained a continuing need to improve the convenience and performance of chest drainage systems and to render such systems very compact. Underwater seal drainage systems as described above require the filling of manometer tubes to levels specified by the physician prior to being connected to the patient and the hospital suction system. Although it is conceivable that such filling could be performed at a manufacturing facility prior to shipment, as a practical matter this would not suffice because frequent adjustments are needed according to the different values of patient suction as dictated by the attending physician. Moreover, the presence of fluid in the various tubes could result in damage to the system during shipment such as because of freezing temperatures or because of leakage. In addition, accuracy of present underwater drainage systems is limited in that the filling of the manometers and the reading of the various gauges must be done visually by observing the liquid level in the respective chambers A reduction in size of the system would offer such benefits as ease of use, ease of storage, less expensive shipping costs, and the reduction in the obstruction between the patient, his or her visitors and the medical staff.

SUMMARY OF THE INVENTION

It is an object of the invention to provide an improved device for regulating the pressure of a gas in one space relative to the pressure of a gas in another space which is communicatable with the first space.

A more specific object is to regulate the pressure of a suction chamber relative to the atmosphere by means of an economical yet effective device.

Another object of the invention is to provide a gas pressure regulating device including an opening through which high pressure air can flow from one spac to a second space at a lower pressure, and means for selectively closing the opening in a smooth manner.

It is another object of the invention to provide an improved system for draining fluid from a portion of the body which can be constructed in a compact and light manner without resort to liquid pressure regulating or monitoring means.

Yet a further object of the invention is the provision of a chest drainage system capable of regulating and measuring suction pressure in an economical, light and effective manner.

An additional object is to provide a system for draining fluid from the body, and for measuring gas flow from the body in an economical and effective manner.

A still further object is to provide a system for draining fluid from a body portion, and for measuring patient negativity in an economical and efficient manner.

It is an object of the invention to provide a system of the preceding type which further can measure maximum patient negativity in an efficient and effective manner.

A further object of the invention is to provide a liquid collection device for reducing the likelihood of spilling liquid collected therein, which device is of simple yet effective construction.

It is a general object of the invention to provide the systems and devices as described above which are practicable, light, compact, and efficient in operation. Other objects will be apparent from the description set forth below and from the appended claims.

The invention in its preferred form includes a pressure regulator including adjoining compartments having an atmospheric pressure chamber, a suction chamber, a divider separating the chambers and having an opening rendering the chambers in communication, a closing member in the suction chamber biased to a position for closing the opening with a force according to the desired suction in the suction chamber, and a damping device for dampening the resultant force on the closing member. The invention in its preferred form includes a fluid drainage system including a suction chamber and a fluid collection chamber, the suction pressure being regulated by a device such as the foregoing, and means for measuring gas flowing through the collection chamber to the suction chamber such as by a flap valve with a dial connected thereto, or a venturi interconnecting the foregoing chambers with a measuring tube assembly connected to the throat of the venturi, or by simply measuring the pressure differential between the chambers. The invention further includes in its preferred form diaphragm assemblies wherein flexing of a diaphragm operates pressure measuring means. Additionally, the invention in its preferred form provides a liquid collection container wherein a fluid conduit in a first chamber has its lowest entrance portion at the horizontal center of gravity of the first chamber.

DESCRIPTION OF THE PREFERRED EMBODIMENTS

Figure 1:
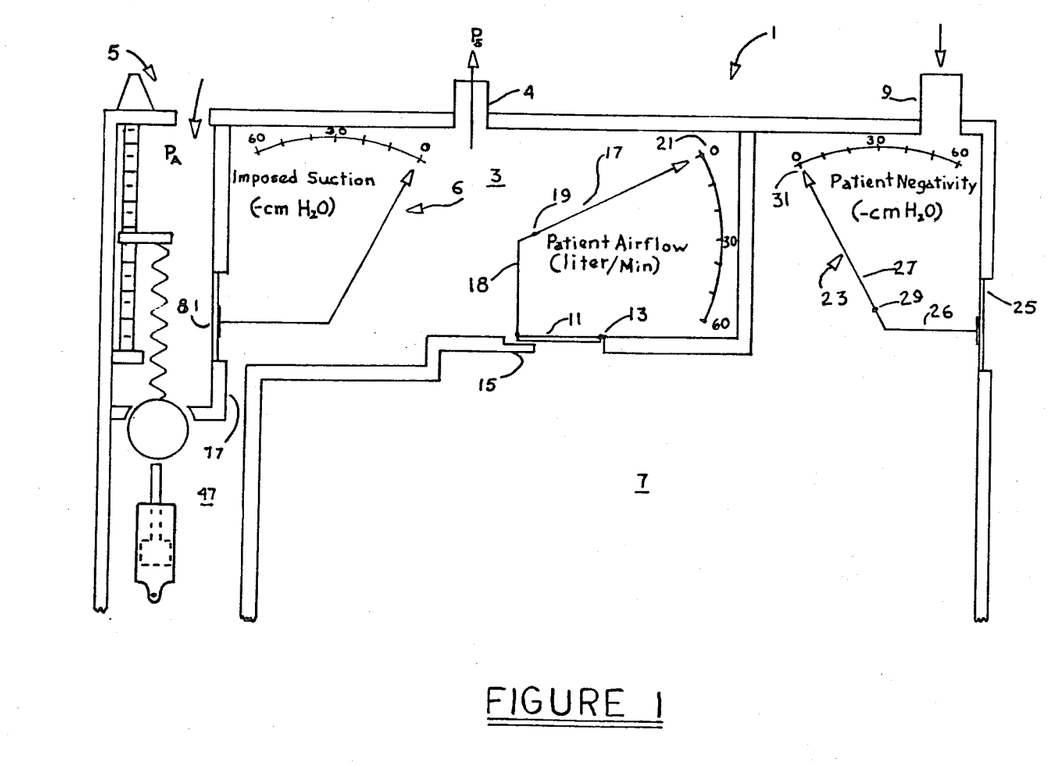
FIG. 1 is a schematic diagram of a chest drainage system according to the invention.

Referring to FIG. 1, a wound drainage system 1 is disclosed comprising a suction chamber 3 from which air can be evacuated by an external vacuum source such as a centrally located vacuum pump in a hospital, a suction port 4 for interconnecting chamber 3 with the external vacuum source, a suction regulator 5 for controlling the pressure in chamber 3, a suction measuring device 6, a collection chamber 7 for collecting fluids withdrawn from a patient, and an inlet port 9 for connecting chamber 7 to the patient. A patient airflow flap valve 11 mounted on a hinge 13 extends over a patient air flow port 15 between collection chamber 7 and suction chamber 3. Air evacuated from a patient through inlet port 9 passes through port 15 whenever the pressure in chamber 7 exceeds that in chamber 3, and the extent of that air flow is reflected by the amount flap valve 11 opens. Valve 11 is configured to close and seal port 15 when the pressure in suction chamber 3 exceeds that in collection chamber 7. A dial 17 mounted on a pivot 19 and movable by a push rod 18 attached to flap valve 11 cooperates with a calibrated scale 21 to indicate the patient air flow rate (generally in liters per minute) through port 15 according to the extent valve 11 opens. When it is a pleural chest cavity being drained, the patient air flow is usually the result of air flowing through a hole in the patient's lung into chamber 7. Suction chamber 3 communicates with suctin regulator 5 via a passage 77.

Occasionally, as when a hole in the patient's lung closes during the drainage process, chamber 7 develops a pressure even more negative than the control suction of suction chamber 3, and flap valve 11 locks shut to isolate the two chambers from each other. It is important for the medical personnel to know the extent of that negativity, and a patient negativity measuring device 23 is provided for this purpose. Device 23 includes a patient negativity diaphragm 25 extending over an opening in the outer wall of chamber 7, a push rod 26 attached to diaphragm 25 and a dial 27 mounted on a pivot 29 movable by push rod 26 for cooperating with an appropriately calibrated scale 31. When the atmospheric pressure outside of chamber 7 exceeds the air pressure in chamber 7, diaphragm 25 flexes inwardly, rotating dial 29 clockwise according to the amount the diaphragm flexes to measure and indicate the extent of patient negativity. The pivot point of dial 27 or the connection point to push rod 26 can be equipped with a spring to urge the dial back to its zero position if a non-linkage connection is preferred.

Figure 2:
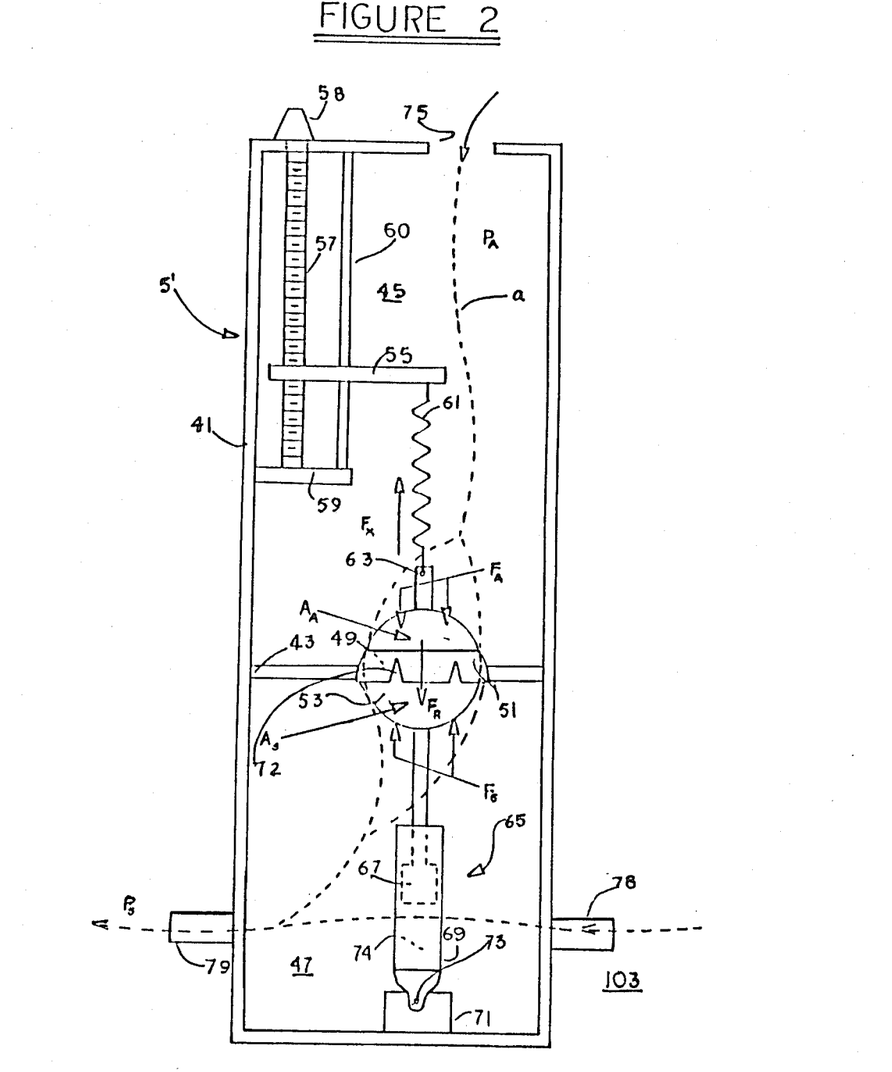
FIG. 2 is a schematic diagram of a suction regulator according to the invention.

The regulation and measurement of the suction in chamber 3 are important functions of system 1. Suction regulator 5 for performing these functions is shown both in FIG. 1 and in further detail (in slightly modified form) as regulator 5 in FIG. 2. (The suction regulator in FIG. 2 is shown as an independent unit which would be modified for a particular application such as incorporation in the system of FIG. 1.) Suction regulator 5 includes a wall 41; a horizontal partition 43 dividing regulator 5 into an upper chamber 45 and a lower chamber 47; an opening 49 in partition 43 in which is seated a collar 51, the collar being a section of a sphere and having a diameter which increases from top to bottom; a light ball 53 whose diameter is slightly more than the diameter of the sphere of which collar 51 is a section so that the ball can fit and be seated in the collar but not pass upwardly through it; a cantilever support arm 55 having a threaded bore through which extends a threaded bolt 57 with an adjustment knob 58 (which could have detents to avoid accidental changes) and disposed on a support shelf 59; a vertical guide rod 60 mounted between shelf 59 and the top wall of the unit for extending through a smooth bore in arm 55 to guide the vertical movement of arm 55; a spring 61 attached at one end to a flange 63 on ball 53 and at its other end to support arm 55 for biassing ball 53 upwardly; and a dashpot 65 composed of a piston 67 attached to ball 53 and a cylinder 69 receiving the piston in sliding engagement and mounted on a support block 71 by means of a pivot 73. Collar 51 preferably includes a set of notches 72 for enhancing the stabilizing effect of collar 51 on ball 53 as air flows between the collar and the ball. A piston chamber 74 is defined between the head of piston 67 and the closed bore of cylinder 69. Atmospheric air flow at pressure $P_A$ enters chamber 45 through an entrance port 75. Lower chamber 47 includes an entrance port 78 from a chamber 103 at subatmospheric pressure such as the pressure collection chamber 7, and is connected to the hospital suction source through a port 79 at pressure $P_S$. The path of flow is shown by the dotted arrows "a".

Figure 3:
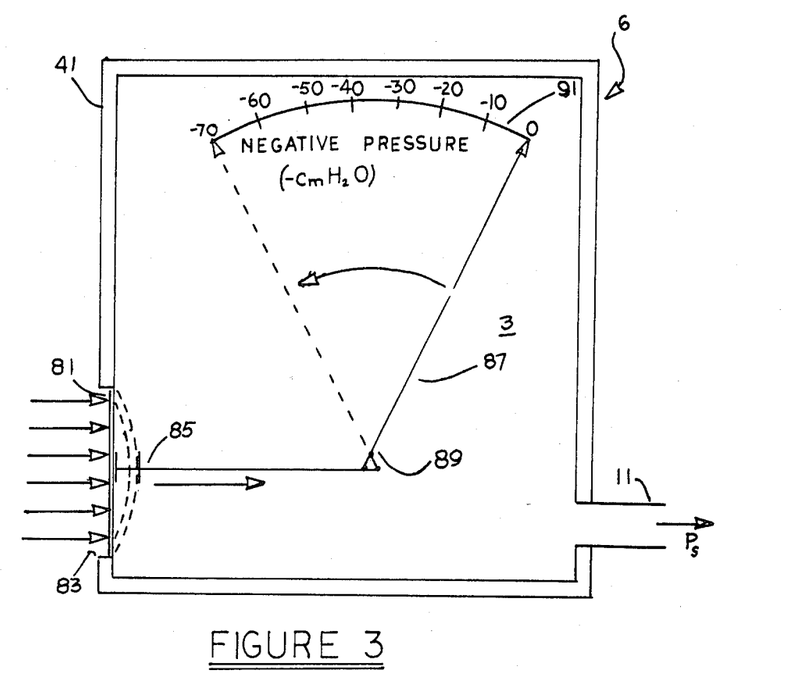
FIG. 3 is a schematic diagram of a device according to the invention for measuring suction pressure in suction chambers such as those of the devices in FIGS. 1 and 2.

The gauge pressure in suction chamber 3 is measured by negative pressure gauge 6 which is shown in detail in FIG. 3. Gauge 6 includes a diaphragm 81 which covers an opening 83 in wall 41 between the upper chamber (which is at atmospheric pressure) of suction regulator 5 and gauge 6 (which is located in suction chamber 3), and a push rod 85 attached at one end to diaphragm 81 and at its other end to a dial 87. Push rod 85 should be light in weight to avoid drooping of the diaphragm. Dial 87 is mounted on a pivot 89 and has a free end which is movable across a negative pressure scale 91 shown calibrated in cm. of water. Diaphragm 81 flexes as shown in dotted lines according to the pressure differential between the pressure in chamber 3 and atmospheric pressure $P_A$ in chamber 45 (i.e. gauge pressure), and such flexure is reflected in the linear movement of push rod 85. Push rod 85 in turn pivots dial 87 about pivot 89 to reflect the negative pressure on scale 91. (If the short end of the dial lever arm 87 which is shown below pivot 89 is doubled back to extend in the same direction from pivot 89 as the long part of dial 87, the direction of movement of the dial and its corresponding scale can be reversed. Also, the direct coupling of the push rod to the dial for effecting dial rotation could be replaced with magnetic drag between the end of the dial and the diaphragm push rod. Likewise, the push rod and dial could be connected through a gear train with the gear ratio set to any value to accomodate different deflection or diaphragm sensitivities expected under different parameters.)

The operation of suction regulator 5' as depicted in FIG. 2 will now be explained. During the operation of system 1, the attendant will have selected some desired negative pressure in chamber 3. Knob 58 is turned to raise or lower cantilever arm 55 to achieve a desired elongation of spring 61 according to the negative pressure sought. Normally, the pressure in upper chamber 45 will exceed the pressure in chamber 47, and the resultant force $F_A$ from atmospheric pressure $P_A$ applied over the exposed surface area $A_A$ of ball 53 in chamber 45 exceeds the resultant force $F_S$ from the negative or suction pressure $P_S$ applied over the area $A_S$ of ball 53 in chamber 47. However, as long as the upward forces $F_X$ of spring 61 and $F_S$ exceed $F_A$, the resultant force $F_R$ ($=F_X-(F_A-F_S)$) is upward and it causes ball 53 to remain seated in collar 51 to seal off chamber 47. Whenever $F_R$ is downward because the atmospheric pressure force $F_A$ exceeds the combined spring force F and suction force $F_S$, ball 53 is unseated and atmospheric air flows through opening 49 until the resultant force $F_R$ is again upward and ball 53 returns to its seated position. The following indicates the various force values:

$$F_X = Kx$$

where
$F_X$ = spring force
$K$ = spring constant
$x$ = spring deflection $$F_A = A_A P_A$$

where
$F_A$ = atmospheric air pressure force on ball 53
$A_A$ = area of the portion of ball 53 in chamber 45
$P_A$ = atmospheric pressure $$F_S = A_S P_S$$

where
$F_S$ = suction air pressure force on ball 53
$A_S$ = area of the portion of ball 53 in chamber 47
$P_S$ = suction air pressure $$F_R = F_X - (F_A - F_S)$$

where
$F_R$ is the resultant of the preceeding forces

The foregoing force analysis is actually slightly simplified since the respective forces are integrals of the respective vertical pressure components over the surfaces of the ball to which those pressures are applied.

Suction regulator 5 as described thus far would provide for the rapid modulation of ball 53 as the pressure differential across it varies. In order to reduce this modulation, dashpot 65 is provided. Thus, when resultant force $F_R$ becomes downward, ball 53 does not immediately pop open. Rather, the downward movement of ball 53 urges piston 67 downwardly to compress the air in piston chamber 74. The downward movement of piston 67 is slowed down, since air in chamber 74 compresses slowly and air can only leak out between piston 67 and the inner wall of cylinder 69 slowly. Likewise, when the resultant force $F_R$ is upward, the movement of ball 53 from its open to its closed position is also slowed down. The air leakage about cylinder 69 reduces the effect of friction between the cylinder wall and piston 67.

Figure 4:
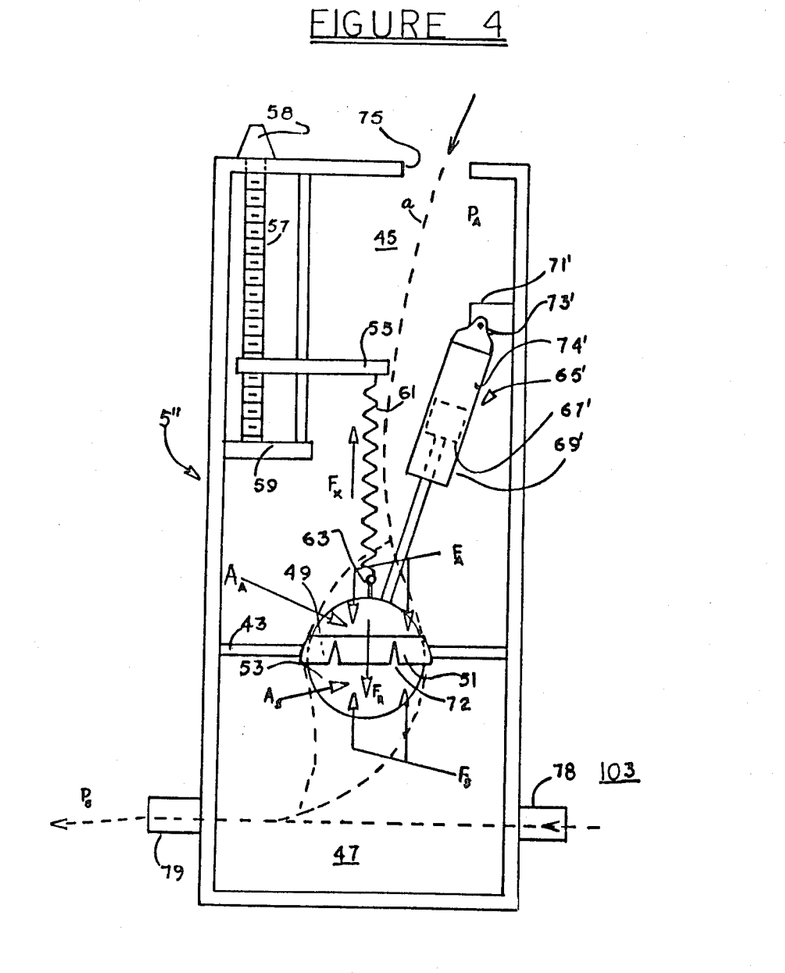
FIG. 4 is a modified version of the device shown in FIG. 2.

When the negative pressure or suction in the lower chamber of the suction regulator is great, a modified suction regulator 5" shown in FIG. 4 is provided according to the invention. This arrangement is very advantageous, because it avoids the drag which could be imposed on piston 67 without a sufficient movement of air around the piston which acts as a lubricant for the piston. In FIG. 4, like parts in the device of FIG. 2 are given like numerals, and reference is made to the previous discussion for a description of them. The main difference between suction regulators 5 and 5" lies in the location of the respective dashpots. In regulator 5", a dashpot 65' is located in atmospheric pressure chamber 45, and includes a piston 67', a cylinder 69' having a piston chamber 74', a support block 71' and a pivot 73' on which cylinder 69' is mounted. Dashpot 65' functions in the manner of dashpot 69, but the increased air flow about piston 67' can avoid the drag referred to above.

As noted above, suction regulators 5' and 5" can be incorporated in systems such as that in FIG. 1, but they also could be incorporated in other chest drainage systems, and in other systems where gas suction must be regulated. For example, such suction regulators could be used at the various parts of a hospital suction system having various ducts serviced by a centrally located suction pump. Since variations of the forces are linear with regard to the change in spring length ($F=Kx$) and air pressure ($F=PA$), adjustments to spring 61 can be made easily to accomodate changes in ambient pressure. The suction regulator according to the invention can also be used for regulating pressures above ambient pressure, such as by admitting atmospheric air to lower chamber 47 and connecting the upper chamber to a source of higher than atmospheric pressure gas. In the latter case, higher than atmospheric pressure gas could be bled to the atmosphere as required. Although the foregoing techniques have been described with a seated ball whose position is varied as the pressure differential across it varies, these techniques could be used with other gas port closing means such as hinged doors.

Figure 5:
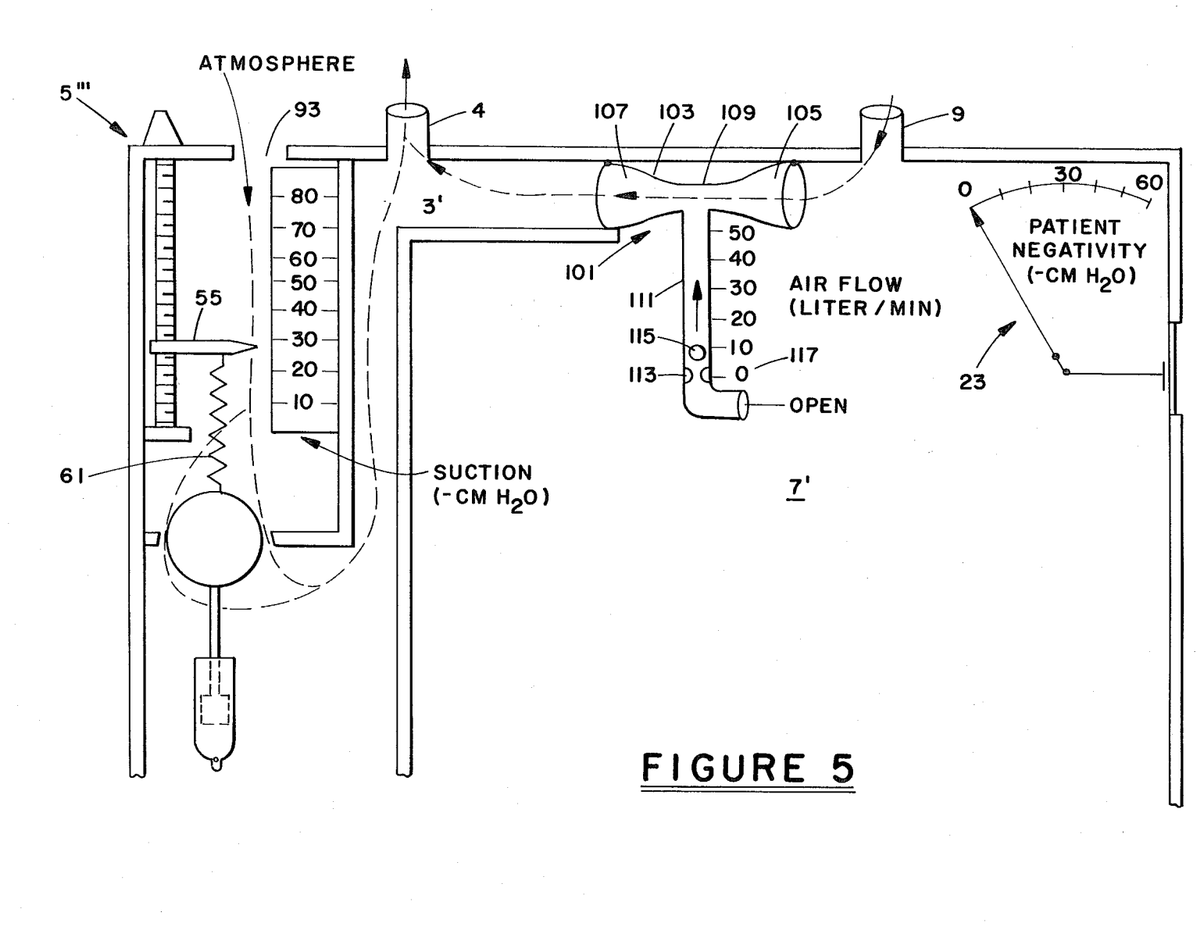
FIG. 5 is a modified version of the system depicted in FIG. 1.

Referring next to FIG. 5, a modified wound drainage system according to the invention is shown. The latter system includes a suction source port 4 as described earlier, a suction regulator 5'" like that of FIG. 1 but lacking suction measuring device 6, a suction chamber 3' and a collection chamber 7' similar to the chambers 3 and 7, respectively, of FIG. 1, and an inlet port 9. A scale 93 calibrated in negative pressure (suction) values is provided for cooperation with cantilever arm 55 to enable the setting of the force of spring 61 according to the desired suction in chamber 3'. In order to measure patient air flow, a venturi device 101 is provided. Device 101 includes a venturi tube 103 having inlet and outlet ports 105 and 107, respectively, and a throat 109. An L-shaped tube 111 opens into throat 109, having a constriction 113 near its vertical base and a light ball 115 disposed in the tube between constriction 113 and throat 109. The level of ball 115 in tube 111 is indicative of the flow rate of air through venturi tube 103, and a scale 117 is calibrated to show the value of that air flow rate. Because of the pressure differential between suction chamber 3' and collection chamber 7', air from the patient flows into port 9, through venturi tube 103, into chamber 3' and out port 4. As the air flows through throat 109, the air velocity increases and its pressure drops in the throat, the pressure drop being directly proportional to the rate of air flow. Ball 115 assumes a level in tube 111 according to the air pressure differential between throat 109 and chamber 7' and the air flow can be read from scale 117.

Figure 6:
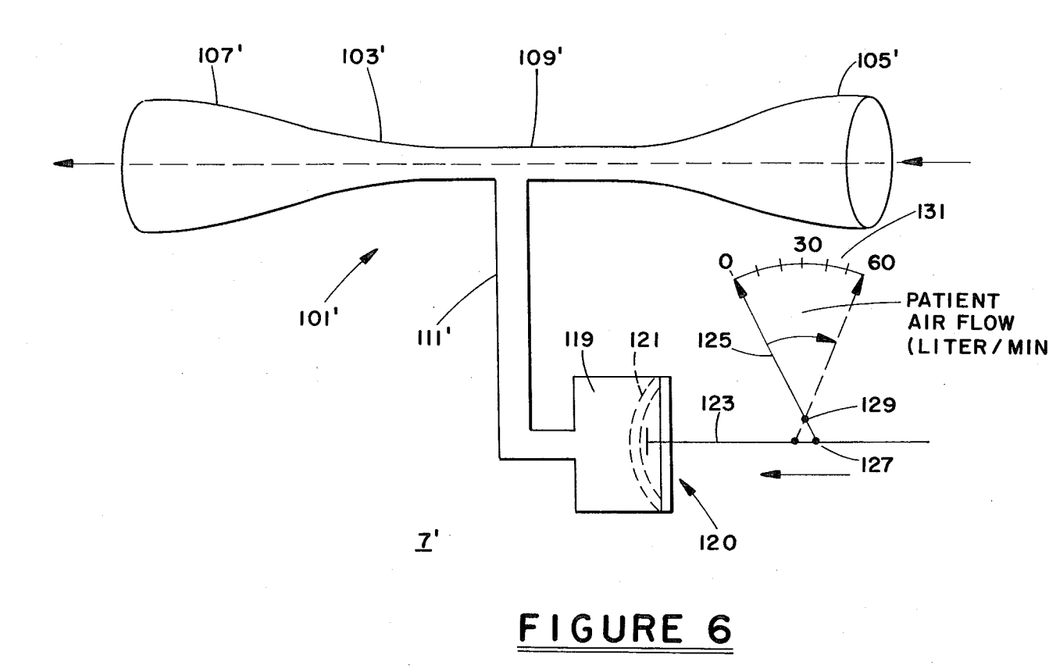
FIG. 6 shows in schematic form a modified version of the venturi device shown in the system of FIG. 5.

A modified version of the venturi tube device is shown in FIG. 6. Here, the vertical tube and ball arrangement is replaced with a diaphragm assembly. A venturi tube assembly 101' is thus provided which includes a venturi tube 103' having an inlet 105' and outlet 107', and a throat 109'. An L-shaped tube 111' communicates with throat 109' and is connected to a chamber 119. Patient air flow is measured by a patient air flow gauge 120. Gauge 120 includes a diaphragm 121 mounted in an opening in one of the walls defining chamber 119, diaphragm 121 flexing to the dotted line position according to the extent of a pressure differential between the low pressure in chamber 119 an the higher pressure in chamber 7'. A rod 123 is attached to diaphragm 121 and is movable therewith as shown by the arrow. A dial 125 is attached to the end of rod 123 by means of a swivel joint 127, and is rotatable about a pivot 129 in response to movement of diaphragm 121. A scale 131 is disposed adjacent the free end of dial 125 and is calibrated to indicate the pressure air flow rate in liters per minute according to the position of dial 125.

Figure 7:
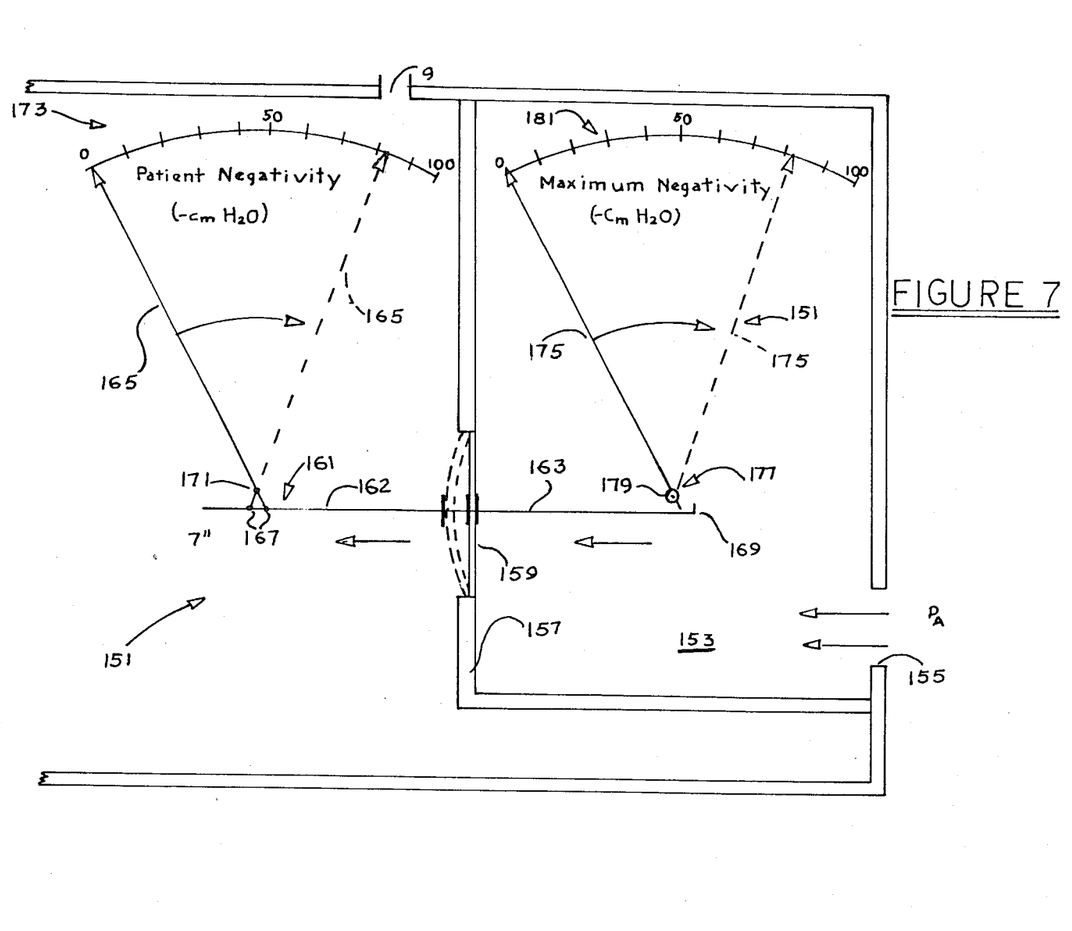
FIG. 7 is a schematic diagram of a device for measuring patient negativity and maximum patient negativity in drainage systems such as those of FIGS. 1 and 5.

As mentioned earlier, it is often important to detect patient negativity (sub-atmospheric pressure in the patient) and store the maximum value of patient negativity. A mechanism 151 for providing these measurements is depicted in FIG. 7. This mechanism includes walls defining a collection chamber 7" which communicates through port 9 with the source of the pressure being measured in the patient, an atmospheric pressure chamber 153 which communicates with the ambient air through a port 155, and a wall 157 between chambers 7" and 153 and having an opening which is sealed by a diaphragm 159. A rod 161 is attached to and has components 162 and 163 extending in opposite directions from diaphragm 159. Diaphragm 159 is flexible and moves between the unflexed position shown in solid lines and the flexed position shown in dotted lines. Rod portion 62 is attached to a dial 165 by means of a swivel joint 67, and rod portion 163 terminates in an upstanding flange 169. Dial 165 rotates clockwise about a pivot 171 in response to the flexing of diaphragm 159, and a scale 173 at the free end of dial 165 indicates the instantaneous patient negativity in appropriate units such as -cm. of water.

A dial 175 is pivotally mounted on a pivot mechanism 177 which retains the dial in its position of maximum (clockwise) rotation. Mechanism 177 can for example be a ratchet device. Flange 169 engages the lower end of dial 175 and rotates the dial in the clockwise direction when diaphragm 159 flexes according to the amount by which the atmospheric pressure in chamber 153 exceeds the patient pressure in chamber 7". A knob 179 is provided for releasing dial 177 to allow its resetting to 0. A scale 181 preferably calibrated in the manner of scale 173 cooperates with dial 175 to indicate the maximum patient negativity during any period of time prior to the release of dial 175 by knob 179.

Figure 8:
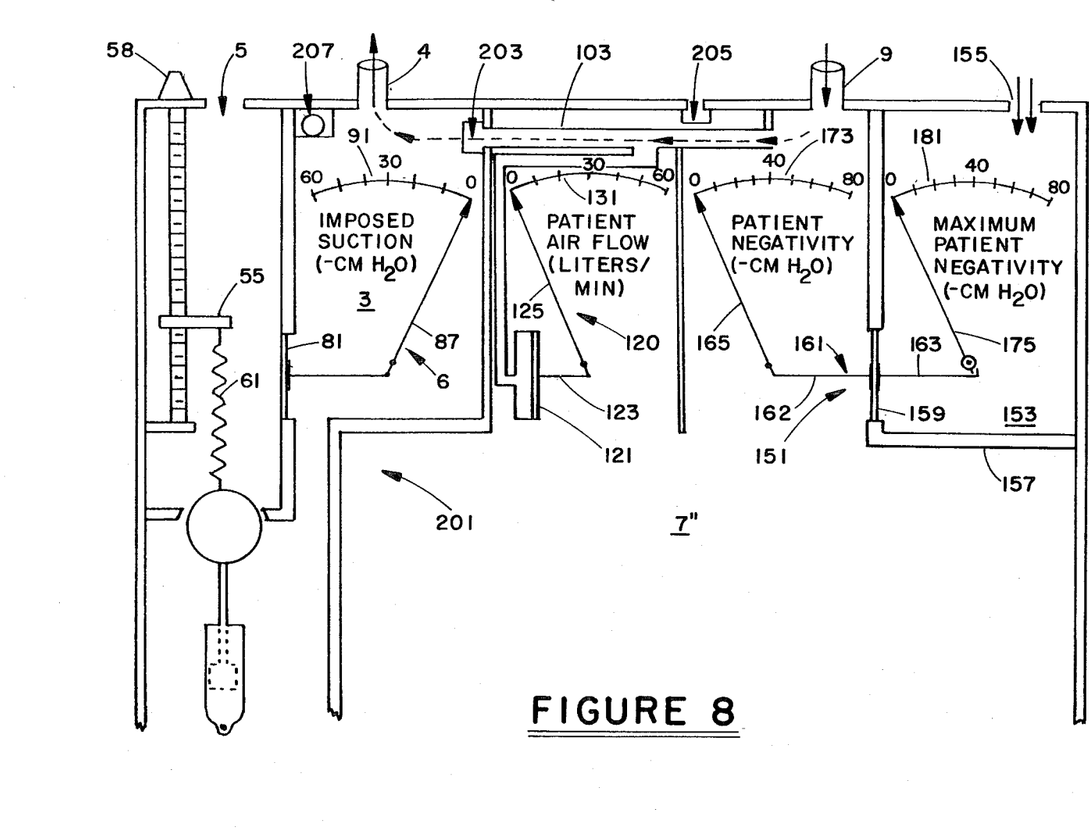
FIG. 8 shows in schematic form a wound drainage system according to the invention incorporating the devices shown in FIGS. 1, 6 and 7.

A chest drainage system 201 incorporating suction regulator 5 used with suction measuring device 6 of FIG. 1, patient air flow gauge 120 of FIG. 6, and the patient negativity and maximum patient negativity measuring device of FIG. 7, is shown in FIG. 8. To operate system 201, port 4 is connected to the suction source, and the user rotates knob 58 to preset cantilever arm 55 to adjust the length of spring 61 according to the suction setting desired. Appropriate tubing from the patient's pleural cavity is connected to inlet 9. When the gas pressure in the pleural cavity is greater than the pressure in suction chamber 3, gas flows into inlet 9, through tube 103 from which it exists via a one way valve 203, and out suction port 4. The negative or suction pressure in suction chamber 3 results in the deflection of diaphragm 81, and the value of the suction pressure is indicated by the position of dial 87 on scale 91 of gauge 6. The patient air flow is reflected in the amount of deflection of diaphragm 121 of patient air flow gauge 120, and this measurement is indicated by the position of dial 125 on scale 131. If the pressure in the patient's pleural cavity is subatmospheric, diaphragm 159 flexes to the left as viewed in FIG. 7, and this results in the clockwise rotation of dial 165. The value of patient negativity is reflected in the position of dial 165 on scale 173. The maximum negativity is shown by the position of dial 175 on scale 181.

Chest drainage system 201 includes a negativity release valve 205 This valve vents atmospheric air into collection chamber 7" when the patient negativity exceeds the closing bias on valve 205. Valve 205 can be adjusted by means of spring tension in the manner of regulator 5, a weighted ball if a fixed value is acceptable, or a button actuated release. When the patient negativity is less than (i.e. more negative) the suction in suction chamber 3, air cannot flow from the suction chamber into tube 103 because one way valve 203 closes tube 103. A positive pressure vent 207 is provided to open suction chamber 3 to the atmosphere to avoid a build-up of positive pressure air (i.e. above atmospheric pressure air) in chamber 3 should there be a failure of the suction source. The drainage systems, suction regulators and other devices provided by the present invention offer numerous advantages over the prior art. The system in its various forms is dry, and thus avoids the various shortcomings of the systems relying on water for regulating and measuring the various pressure values. The system and its components are of very simple construction, contributing to the ease of manufacture, use and general economy thereof. The system and its components are compact and light, rendering it easy to store and use. Yet, despite its simplicity, it is highly effective in use.

It would be advantageous to reduce the likelihood of spill-over of fluid accumulated in the collection chamber of the systems described above as well as in such systems as the Pleur-evac mentioned earlier. Such spill-over involves the spilling of fluids from the collection chamber into adjoining chambers of a wound drainage system. It can occur because of the tilting, shaking or dropping of the chest drainage unit by persons attending the patient, or because the unit, the patient or the patient's bed is moved excessively. The device described below addresses the spill-over problem.

Figure 12:
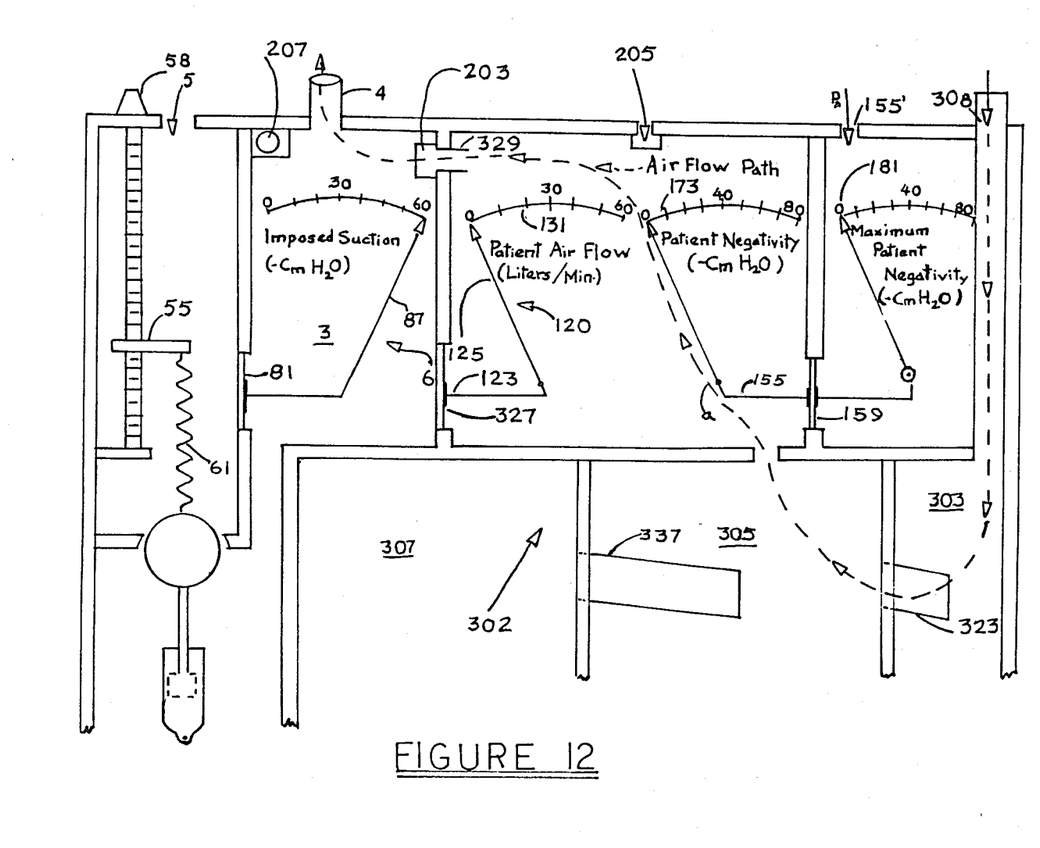
FIG. 12 is a schematic diagram of the system of FIG. 8, modified to include an anti-spill device of the type shown in FIGS. 9–11.

Referring first to FIG. 12, a system 302 very similar to chest drainage system 201 of FIG. 8 is shown. However, the single collection chamber of system 201 has been replaced by three collection chambers 303, 305 and 307 as described below, a relocated port 155' to the atmosphere is provided, and a passage 308 for connecting the unit to the patient replaces port 9 from systems described previously.

Figure 9:
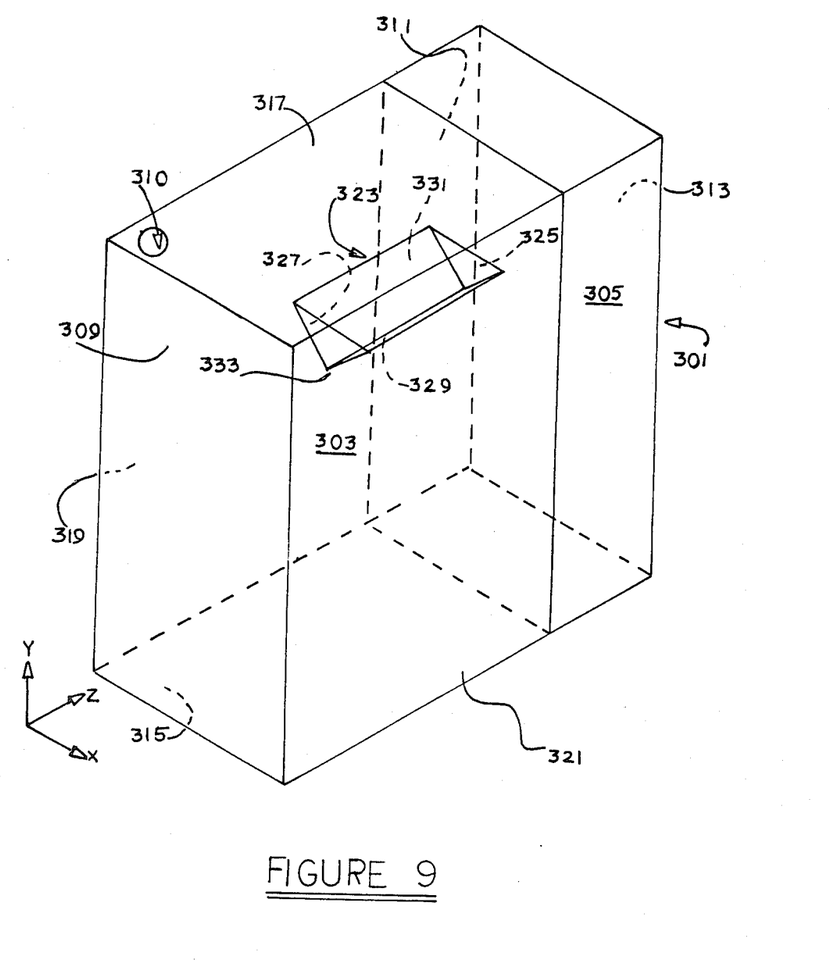
FIG. 9 is a schematic diagram, in perspective, of an anti-spill device according to the invention.
Figure 10:
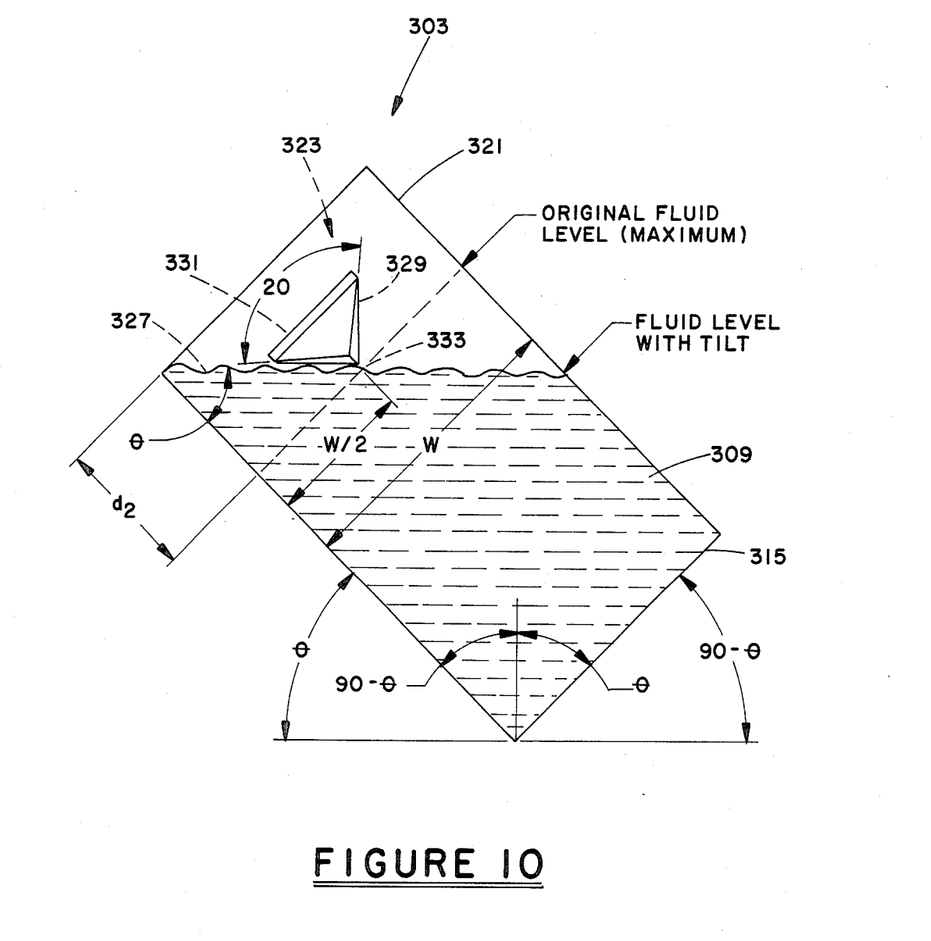
FIGS. 10 and 11 are side and front views, respectively, of the device shown in FIG. 9.
Figure 11:
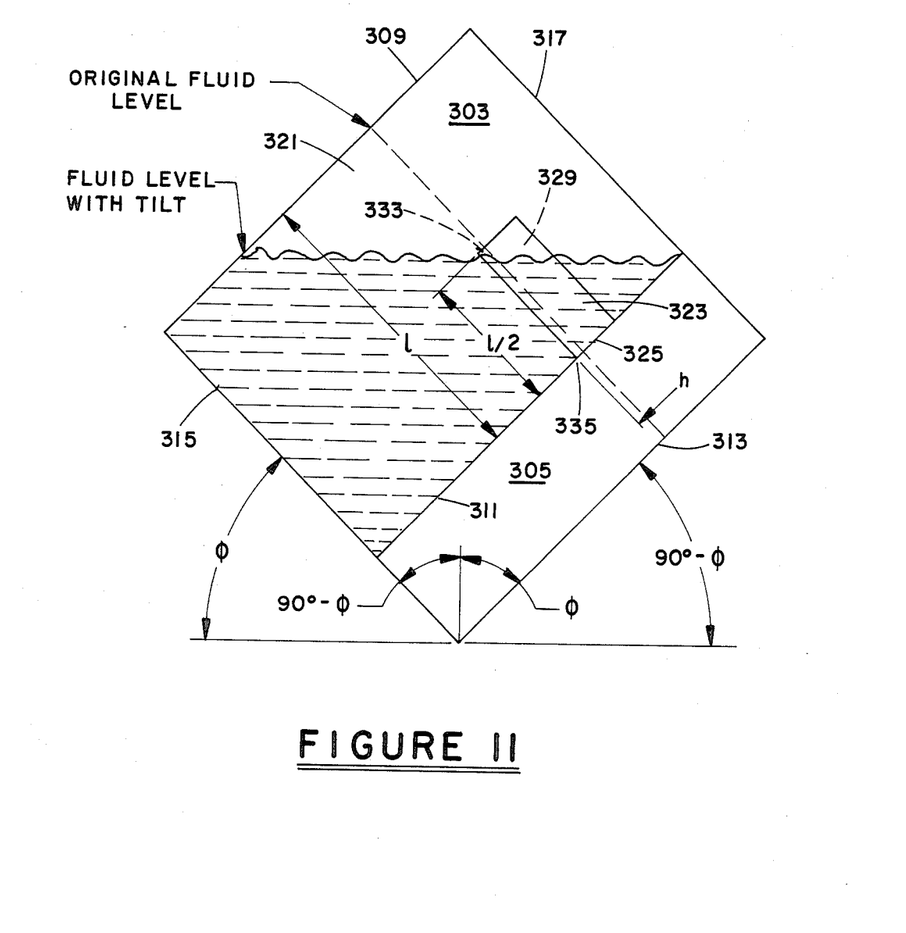

Referring next to FIGS. 9–11, anti-spill device 301 pursuant to an aspect of the invention is shown. Device 301 is composed of vertical side walls 309, 311 and 313, which with a bottom wall 315, a top wall 317, rear wall 319 and a front wall 321 define adjoining prismatic fluid collection chambers 303 and 305. A fluid entrance port 310 is located in top wall 317. A triangular conduit 323 extends perpendicularly from a triangular opening 325 in side wall 311. Conduit 323 is composed of side walls 327 and 329, and a top wall 331. The lowermost entrance to conduit 323 is a point 333 at the juncture of walls 327 and 329 and an imaginary plane across that entrance. Point 333 is located midway both between rear wall 319 and front wall 321 and a distance −1" from side wall 309. The measurement "1" is optional but is chosen to move point 333 as close as possible to side wall 309 without interfering with fluid flow, blood clots or the like. Since the diameter of the entrance tubes is normally in the range of ⅜", the minimum length of "1" will be comparable with that dimension as well. The positioning of the lowest entrance point of the conduit from chamber 303 to chamber 305 effectively enables the maximum amount of rotation of chamber 303 in either the x-axis or z-axis for any given amount of fluid in chamber 303 before there can be any spill-over of fluid from chamber 303 to chamber 305. In order to maintain a predetermined maximum angle of tilt or rotation before spilling occurs (angle of anti-spill tilt) as the fluid level rises in chamber 303, the minimum distance of point 333 below upper wall 317 will depend on, and can be calculated from, the other dimensions of chamber 303.

The manner in which the construction of the device 301 reduces spillage of fluid from chamber 303 is shown in FIGS. 10 and 11. Referring first to FIG. 10, chamber 303 is shown tilted such that rear wall 319 is at an angle $\theta$ from horizontal, angle $90-\theta$ being the maximum amount of tilt permissible in that axis for preventing spilling of the fluid in chamber 303 under all conditions of fluid level. Walls 327 and 329 intersect at an angle $2\theta$. Collection chamber 303 can be rotated by an angle $90°-\theta$ about an axis perpendicular to wall 309 before any fluid can enter conduit 323 and flow out of chamber 303. Were point 333 any closer to either of walls 319 or 321, spill-over would occur sooner for rotation in one direction or the other. By decreasing the angle of intersection of walls 327 and 329, the greater the amount chamber 303 can be tilted before spill-over begins. The distance of point 333 from top wall 317 for a maximum permissible amount of rotation or tilt of chamber 303 just prior to spillage can be calculated as follows:

$$\tan \theta = \frac{w/2}{d}$$

$$d = \frac{w}{2 \tan \theta}$$

where $90-\theta$ = max. angle of rotation of chamber 303 about the z axis before spillage as shown in FIG. 10 w = distance between side walls 319 and 321 d = the minimum distance of point 333 from top wall 317 for a given maximum angle of rotation at original maximum fluid level.

If point 333 were any closer to top wall 317 than d, the fluid would have insufficient room to travel up side wall 319 (or wall 321) and the fluid would be forced to the right (or left) before rotation of 90°−θ had occurred. That is, spillage would occur sooner than if point 333 were located closer to the top wall than at the distance d as calculated above.

With regard to FIG. 11, it can be seen that chamber 303 can be rotated around the x-axis well in excess of the indicated tilt angle $\phi$ before any fluids enter conduit 323 leading to the adjacent collection chamber 305. As indicated earlier, by moving point 333 closer to side wall 309, the amount chamber 303 can be rotated clockwise about an axis perpendicular to wall 321 (x-axis) is increased, in fact, if the calculation for d (as derived above) is satisifed, $\phi$ can be increased to 90° with no danger of spillover. However, for counterclockwise rotation, fluid would begin entering the conduit sooner but would not spill over into chamber 305 until the fluid level exceeds point 335. Finally, should fluid entering the conduit in any way pose a problem for certain applications, the conduit length could be shortened to lie midway between walls 309 and 311 and a geometric/trigonometric relationship can be formulated for rotation about the x-axis similar to that for rotation about the z-axis. In this case, point 333 is situated at the horizontal center of gravity of chamber 303.

FIGS. 9-11 show the collection chamber arrangement to include two chambers. Any number of chambers can be arranged adjacent each other with spill-over reducing conduits 323 provided therein. In FIG. 12, three such chambers 303, 305, and 307 are provided, with chambers 303 and 305 having spill-over reduction conduits 323 and 337, respectively, incorporated therein.

Referring again to FIG. 12, another means for indicating patient air flow is shown. Accordingly, a diaphragm 327 is provided in the wall separating the collection chamber and suction chamber 3. A conduit 329 having a one way valve 203 is also provided in that wall. Air flow follows the path shown by the dotted arrow "a". Since the transport of air and the volume of flow are always associated with a pressure differential, diaphragm 327 flexes according to a pressure differential across it to indicate patient air flow on gauge 120 as discussed earlier.

The invention has been described in detail with particular emphasis on the preferred embodiments thereof, but it should be understood that variations and modifications within the spirit and scope of the invention may occur to those skilled in the art to which the invention pertains.

We claim:

1. A system for draining fluids from a portion of the body, said system comprising:
    collection means for receiving fluids from the body, said collection means including an inlet port for admitting fluids from the body to said collection means;
    a suction chamber communicatable with said collection means, said suction chamber being connectable to a suction source;
    a suction regulator for controlling the pressure in said suction chamber, said suction regulator including
    a first compartment having a first chamber communicating with the atmosphere;
    a second compartment having a second chamber communicating with said suction chamber;
    first dividing means dividing said first chamber from said second chamber, said first dividing means including an opening for putting said second chamber in communication with said first chamber;
    first closing means movable between an opening position for opening said opening and a closing position for closing said opening; and
    biasing means for biasing said closing means towards the closed position with a force which establishes a force equilibrium across said closing means when the force resulting from the application of the desired pressure to said closing means occurs;
    second dividing means for dividing said collection chamber from said suction chamber, said second dividing means comprising an entrance port for admitting gases from said collection chamber into said suctiion chamber;
    second closing means movable between an opening position for opening said entrance port and a closing position for closing said entrance port; and
    second measuring means for measuring the rate of flow of gas through said entrance port.

2. The invention according to claim 1 wherein said second closing means comprises a flap valve.

3. The invention according to claim 2 wherein said second measuring means comprises dial means operatively connected to and movable with said flap valve in proportion to the rate of flow of gas through said entrance port, and a scale calibrated to cooperate with said dial means to indicate the rate of flow of gas through said entrance port.

4. A system for draining fluids from a portion of the body, said system comprising:
    collection means for receiving fluids from the body, said collection means including an inlet port for admitting fluids from the body to said collection means;
    a suction chamber communicatable with said collection means, said suction chamber being connectable to a suction source;
    a suction regulator for controlling the pressure in said suction chamber, said suction regulator including
    a first compartment having a first chamber communicating with the atmosphere;
    a second compartment having a second chamber communicating with said suction chamber;
    first dividing means dividing said first chamber from said second chamber, said first dividing means including an opening for putting said second chamber in communication with said first chamber;
    first closing means movable between an opening position for opening said opening and a closing position for closing said opening; and
    biasing means for biasing said closing means towards the closed position with a force which establishes a force equilibrium across said closing means when the force resulting from the application of the desired pressure to said closing means occurs;l
    venturi means for admitting gases from said collection chamber into said suction chamber rate a flow rate according to the pressure differential between said collection chamber and said suction chamber; and
    gas flow measuring means for measuring the gas flow rate through said venture means.

5. The invention according to claim 4 wherein said venturi means comprises a venturi tube having venturi entrance and exit ports and a throat, and a measuring tube communicating with said throat, a bobbing member disposed in said measuring tube for assuming a position according to the gas flow rate through said venturi tube, and a scale calibrated to cooperate with said bobbing member to indicate the gas flow rate through said venturi tube.

6. The invention according to claim 4 wherein said venturi means comprises a venturi tube having venturi entrance and exit ports and a throat, and walls defining a measuring chamber communicating with said throat, said walls including an air flow diaphragm for flexing in proportion to the air flow rate through said venturi tube.

7. The invention according to claim 6 and further including gas flow dial mean movable with said air flow diaphragm, and a gas flow scale calibrated to cooperate with said gas flow dial means to indicate the gas flow rate through said venturi tube.

8. The invention according to claim 7 wherein said maximum negativity means comprises:
   maximum negativity dial means movable according to the maximum flexing of said second diaphragm means in response to the maximum patient negativity responded to by said second diaphragm means,
   a maximum negativity scale calibrated to cooperate with said maximum negativity dial means to indicate the maximum negativity; and
   dial control means for moving said maximum negativity dial means to a position indicative of the maximum negativity.

9. The invention according to claim 8 and further including
   third dial means operatively connected to said second diaphragm means for moving according to the flexing of said second diaphragm means, and a third scale calibrated to cooperate with said third dial means to indicate the value of patient negativity.

10. A system for draining fluids from a portion of the body, said system comprising:
    collection means for receiving fluids from the body, said collection means including an inlet port for admitting fluids from the body to said collection means;
    a suction chamber communicatable with said collection means, said suction chamber being connectable to a suction source;
    a suction regulator for controlling the pressure in said suction chamber, said suction regulator including
    a first compartment having a first chamber communicating with the atmosphere;
    a second compartment having a second chamber communicating with said suction chamber;
    first dividing means dividing said first chamber from said second chamber, said first dividing means including an opening for putting said second chamber in communication with said first chamber;
    first closing means movable between an opening position for opening said opening and a closing position for closing said opening; and
    biasing means for biasing said closing means towards the closed positiion with a force which establishes a force equilibrium across said closing means when the force resulting from the application of the desired pressure to said closing means occurs;
    said collection means comprising a first container having a collection chamber, a second container, and a conduit connecting said collection chamber and said second container, said conduit having an entrance with a lowermost entrance portion at the horizontal center of geometry of said collection chamber and a triangular cross section, with the intersection of two sides at said entrance forming said lowermost entrance portion.

* * * * *